United States Patent
Ito

[11] Patent Number: 6,139,515
[45] Date of Patent: Oct. 31, 2000

[54] PHIMOSIS CURING APPLIANCE

[75] Inventor: Kanji Ito, Kawaguchi, Japan

[73] Assignee: Wen Tao, Saitama, Japan; a part interest

[21] Appl. No.: 09/365,749

[22] Filed: Aug. 3, 1999

Related U.S. Application Data

[63] Continuation of application No. PCT/JP98/00421, Feb. 2, 1998.

[30] Foreign Application Priority Data

Feb. 3, 1997 [JP] Japan .................................. 9-020528

[51] Int. Cl.$^7$ ...................................................... A61F 13/00
[52] U.S. Cl. ................................................ 602/67; 602/70
[58] Field of Search .................................. 128/95.1, 96.1, 128/97.1, 98.1, 99.1, 100.1; 602/67, 68, 69, 70, 71

[56] References Cited

U.S. PATENT DOCUMENTS

| | | | |
|---|---|---|---|
| 311,570 | 2/1885 | Cronin | 602/70 |
| 792,424 | 6/1905 | King | 602/70 |
| 1,920,648 | 8/1933 | Lane | 602/70 |
| 2,427,428 | 9/1947 | Vitale | 602/70 |
| 5,651,144 | 7/1997 | Li | 602/70 |

FOREIGN PATENT DOCUMENTS

| | | |
|---|---|---|
| 50-96094 | 7/1975 | Japan . |
| 52-77598 | 6/1977 | Japan . |
| 59-36321 | 3/1984 | Japan . |
| 2-46334 | 12/1990 | Japan . |
| 3-27626 | 6/1991 | Japan . |

*Primary Examiner*—Michael A. Brown
*Attorney, Agent, or Firm*—Griffin & Szipl, PC

[57] ABSTRACT

The phimosis curing appliance according to the present invention allows a surplus prepuce in a pseudophimosis condition to be forcedly retracted toward a root of a human penis so that a glans of the penis can be surely kept in an exposed condition for a long time, and the appliance has a simplified structure suitable for standardization and mass production. The phimosis curing appliance 1 comprises an annulus waist holding belt 2 supportable on a human waist; a resiliently stretchable supporting belt 3 suspended from the waist holding belt to form a region through which the human penis extends; a resiliently stretchable traction belt 4 for connecting a rear portion 2b of the waist holding belt and the supporting belt; and a scrotum biasing zone 5 provided in a joint area of the supporting belt and the traction belt. An upper end portion of the supporting belt is connected to the waist holding belt and the scrotum biasing zone is drawn inward of the human groin by the traction belt.

6 Claims, 6 Drawing Sheets

PHIMOSIS CURING APPLIANCE

This application is a Continuation of International Application No. PCT/JP98/00421, filed Feb. 2, 1998, which claims priority based on Japanese Patent Application No. 9-20528, filed Feb. 3, 1997. The entire disclosures of the above applications are hereby incorporated herein by reference.

TECHNICAL FIELD OF THE INVENTION

The present invention relates to a phimosis curing appliance, and more particularly, to such an appliance having a simplified arrangement which allows a glans of a pseudophimosis penis covered with a prepuce thereof to be kept in an exposed condition for a relatively long time.

BACKGROUND OF THE INVENTION

Generally, a phimosis condition in which the glans is covered with the prepuce includes a true or complete phimosis in which the glans is completely covered with the prepuce, a paraphimosis resulting from a small annulus preputialis (or prepuce opening) and a pseudophimosis in which the glans is normally covered with the prepuce, but can be uncovered upon its erection or the like. It has been suggested that the true phimosis and paraphimosis are relevant to various penile diseases such as inflammation due to smegma, infection disease, and possibly penile cancer. Therefore, many males having true phimosis or paraphimosis symptom, in general, need to take medical treatments such as partial prepuce excision, dorsal penis side opening and the like in medical institutions.

On the other hand, the pseudophimosis generally results from an elongated prepuce relative to the length of a penis so that an extremity of the prepuce covers the glans at least partially, even though the opening of the prepuce is relatively large. In the pseudophimosis condition, the glans is externally exposed during erection of the penis. Therefore, although many males of pseudophimosis are conscious of their pseudophimosis symptom, they may not recognize any particular obstruction or inconvenience in their daily or usual life. Thus, such males of pseudophimosis, in general, do not undergo the aforementioned surgery operations such as prepuce excision or the like.

One plimosis curing appliance for pseudophimosis is disclosed, for example, in Japanese Patent Laid-Open Application No. 62-172948. This phimosis curing appliance is provided with a phimosis band which includes a circular prepuce biasing means for forcibly retracting the prepuce to a position near the root of a penis. When a patient wears the phimosis curing appliance, his prepuce is biased toward the human body or penile root by the edge of a sleeve opening of the prepuce biasing means.

According to such a phimosis curing appliance of the prior art, which merely biases the prepuce toward the human body, the surplus or excessive portion of the prepuce might be able to be deviated and collected between the penis and the scrotum to be held in its retracted position for a short time. However, the phimosis curing appliance of the prior art merely has an arrangement in that the prepuce is forcibly retracted to the penile root by a frictional engagement of the prepuce with the sleeve of the appliance and is held in its retracted position by locally tightening the penile root. Therefore, this kind of phimosis curing appliance cannot surely prevent the prepuce from returning to its original or covering position when it is worn on the human body for a long time. Furthermore, the diameter of the opening of such a phimosis curing appliance is not easily adjustable in dependence on individual penile diameters. Therefore, the phimosis curing appliance of the prior art cannot be standardized and mass produced. It is thus desired to provide a phimosis curing appliance which can inexpensively be made in mass production.

It is therefore an object of the present invention to provide a phimosis curing appliance which can forcedly retract the surplus prepuce of mainly a pseudophimosis penis toward the penile root area and surely keep the glans in an exposed condition for a long time with a simplified arrangement suitable for standardization and mass production.

DISCLOSURE OF THE INVENTION

The present invention provides a phimosis curing appliance comprising an annulus waist holding belt supportable on a human waist; a resiliently stretchable supporting belt suspended from the waist holding belt to form a region through which a human penis extends; a resiliently stretchable traction belt for connecting a rear portion of the waist holding belt and the supporting belt; and a scrotum biasing zone provided in a joint area of the supporting belt and the traction belt, the upper end portion of the supporting belt being connected to the waist holding belt and the scrotum biasing zone being drawn inward of the human groin by the traction belt.

In such an arrangement of the present invention, the waist holding belt is carried by the waist portion of a human body. The traction belt functions to draw the supporting belt inwardly toward the human groin to bias the scrotum biasing zone backward of the human body. The scrotum biasing zone abuts against skins of the scrotum to urge it backwardly relative to the patient's body. As a result, the skins of the scrotum backwardly draw the prepuce of the penis. The surplus prepuce of the penis is biased toward the penile root by the action of the supporting belt and pulled inward of the groin by the scrotal skin, so that a glans of the human penis can be surely and completely exposed for a relatively long time. When the user or patient wears such a phimosis curing appliance, he can obtain various subsidiary advantages such as psychologically overcoming of sexual inferiority complex due to the pseudophimosis, plenitude of physiological ability, substantial increase of the effective length of the penis, increase of the hardness of the penis, improvement of the sensitivity and the like, without taking a surgery excision of the surplus prepuce, since the surplus prepuce can be retracted to the penile root and the glans can be kept to be exposed for a relatively long time.

The phimosis curing appliance belt thus constructed can be standardized and mass produced as in the conventional garments, since it has a structure in which the phimosis curing appliance can relatively easily be adapted for the dimensions of respective individual human bodies owing to its flexibility.

In a preferred embodiment of the present invention, a pair of the supporting belts are located on the opposite sides of the penis insertion region, and the supporting belts form a gap or slit having a predetermined width smaller than the diameter of the human penis. The gap thus formed between the supporting belts defines the penis insertion region. Preferably, a pair of the traction belts are connected to lower ends of the respective supporting belts. A scrotum biasing strip or piece is sewn or adhered to the backsides of the supporting belts at the connection areas of the traction and supporting belts so that the supporting belts are bridged by the scrotum biasing strip.

In one embodiment of the present invention, the supporting belts form a vertically extending gap having a constant width. The width of such a gap is equal to or smaller than 2 mm. According to another embodiment, the gap is slightly divergent in the upward direction.

In a preferred embodiment of the present invention, the scrotum biasing strip is formed by the connection of the supporting and traction belts. The supporting and traction belts are preferably made of the same material and the resilient stretchability in the supporting and traction belts is limited to be lower than that of the waist holding belt.

The present invention also provides a phimosis curing appliance comprising a pair of abutment portions adapted to abut against a skin of a human scrotum for holding a root part of the scrotum; a pair of arms for carrying said abutment portions for resilient deformation; and means for inwardly biasing said arm portions, whereby said abutment portions grasp the skin of the scrotum back and forth so that a prepuce of a human penis is drawn backwardly under a tension of the scrotal skin.

In such an arrangement, the abutment portions hold the scrotum skin therebetween to generally draw the penile prepuce backward of a human body. As a result, the surplus prepuce of the human penis will be drawn toward the penile root and inward of the human groin. Therefore, the glans of the human penis can be surely kept in a complete exposed condition for a relatively long time.

In one embodiment of the present invention, the abutment portion may be formed in a spherical or cylindrical configuration. Preferably, the abutment portions may be covered with any of soft covering materials, such as soft resin, woven fabric or non-woven fabric, which can resiliently abut against the skin of the scrotum. More preferably, the arms may be made of any resiliently deformable material. The resiliency of the arms defines the biasing means. In another preferred embodiment, the base ends of said arms may be interconnected by a pivot means. The pivot means may be provided with the biasing means which is made of a soft spring, rubber or the like for inwardly biasing the arms.

BEST MODE FOR CARRYING OUT THE INVENTION

Phimosis curing appliances according to the preferred embodiments of the present invention will now be described in detail with reference to the accompanying drawings.

Figure 1:
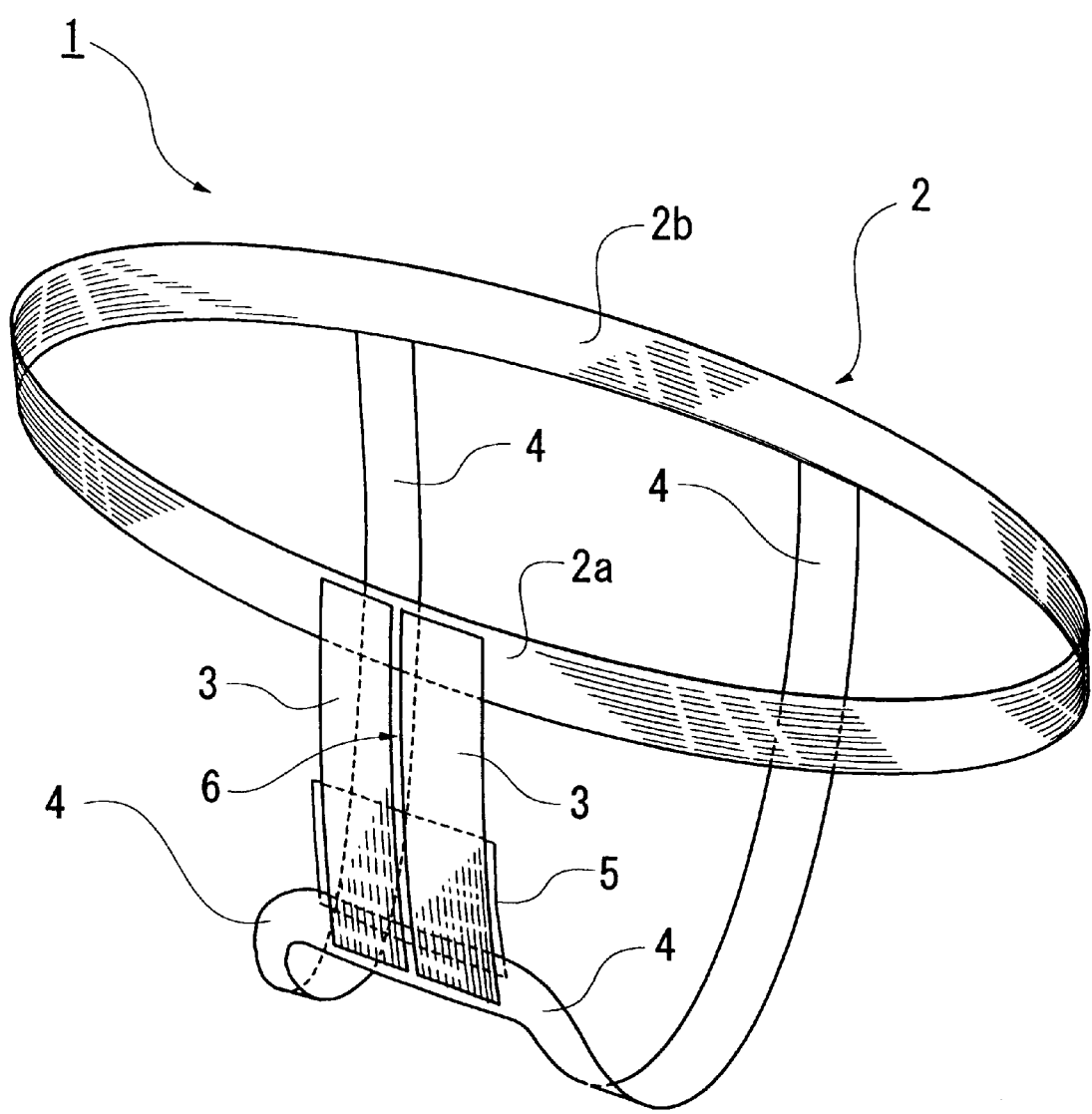
FIG. 1 is a perspective view of the entire phimosis curing appliance according to the first embodiment of the present invention.
Figure 2:
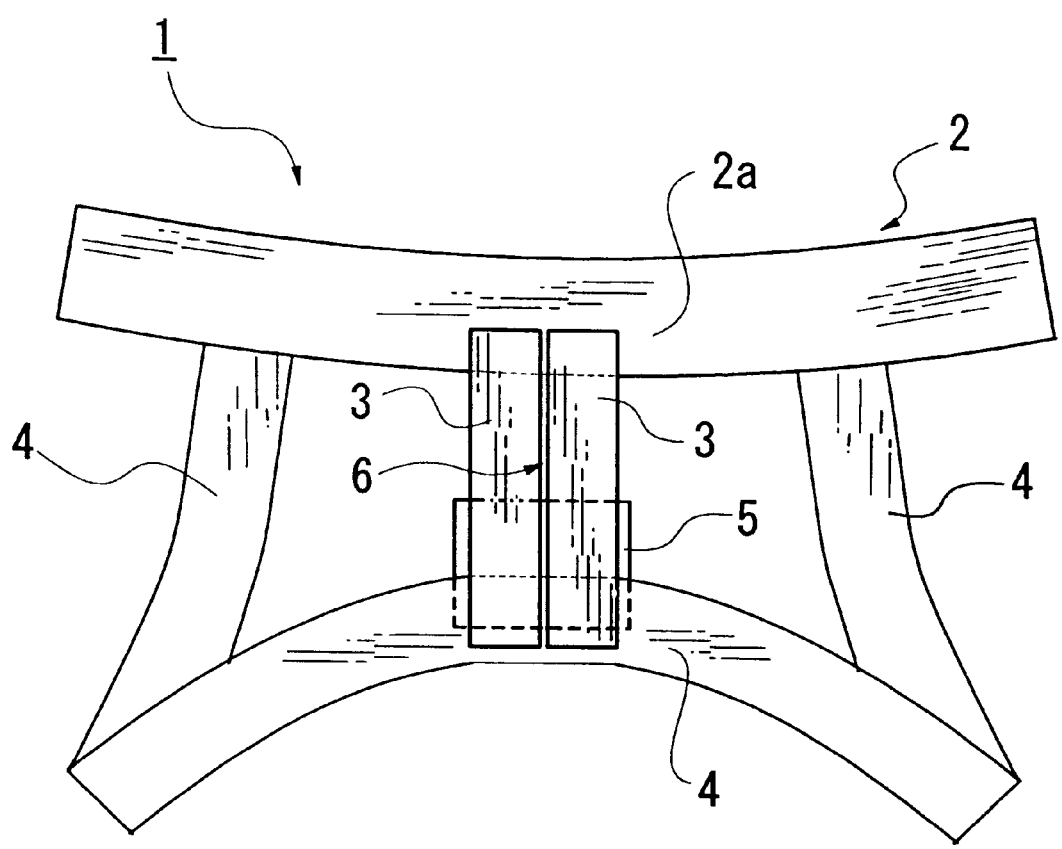
FIG. 2 is a front elevational view of the phimosis curing appliance as illustrated in FIG. 1.

FIG. 1 is a perspective view showing a whole arrangement of the phimosis curing appliance according to the first embodiment of the present invention, and FIG. 2 is a front elevational view of the phimosis curing appliance shown in FIG. 1.

The phimosis curing appliance 1 comprises an annulus-shaped waist holding strip or waist belt 2 attachable on a waist of a patient's body, and a pair of supporting strips or belts 3 downwardly extending from a front portion 2a of the waist holding belt 2. The lower ends of the supporting belts 3 are connected to a rear portion 2b of the waist holding belt 2 by means of a pair of traction belts 4. A scrotum biasing strip 5 engageable with the scrotal skin on a front side of the patient is fixedly secured on backsides of the supporting and traction belts 3, 4 in their joint area.

The waist holding belt 2 is made of a stretchable material containing coated elastic yarns and has the circumferential length corresponding to a perimeter of the human waist section, and a desired elasticity sufficient for bringing the waist holding belt 2 into intimate contact with the waist section when the patient wears the phimosis curing appliance. The rearward ends of the traction belts 4 are fixedly secured to the rear portion 2b of the waist holding belt 2 by sewing or fastening means.

The traction belts 4 extend downwardly from the rear portion 2b along the surface of the patient's buttock and forwardly through the patient's groin, and then, fixedly secured to the lower ends of the respective supporting belts 3 by sewing or fastening means. The traction belts 4 are also made of a resiliently stretchable fabric including coated elastic yarns as in the waist holding belt 2. When the phimosis curing appliance 1 is worn on the patient, the traction belts 4 are slightly stretched to draw the supporting belts 3 inward of the patient's groin with the resiliently restoring force of the traction belts 4.

The supporting belts 3 extend upwardly from the patient's groin along the surface of the patient's abdomen. The upper end of each of the supporting belts 3 is fixedly secured to the front portion 2a of the waist holding belt 2 by sewing or fastening means. The left and right supporting belts 3 are slightly spaced apart from each other to form a gap or slit 6, which has its width smaller than the diameter of the patient's penis. The supporting belts 3 are made of an elastically stretchable fabric containing coated elastic yarns as in the waist holding belt 2 and traction belts 4. The traction and supporting belts 4, 3, which are interconnected to each other in the groin facing region of the phimosis curing appliance, are slightly stretched to extend along the abdomen, groin and buttock of the patient under tension, when the phimosis curing appliance is attached on the patient.

The scrotum biasing strip 5 extends along the backsides of the lower end potions of the supporting belts 3 so as to bridge the belts 3, and it is fixedly secured to the backsides of the lower end portions of the belts 3 and the backsides of the groin facing portions of the traction belts 4 by sewing or fastening means. The scrotum biasing strip 5 is made of a woven or non-woven fabric which can urge the front skin of the patient's scrotum backward of the patient's body and has a soft surface in contact with the skin of the patient's scrotum. The scrotum biasing strip 5 abuts against a front side of the scrotum under the resiliently restoring force of the stretched belts 4, 3, whereby the scrotum biasing strip 5 backwardly biases the scrotum under the limited tension of the traction belts 4. As a result, the patient's scrotum is drawn into the patient's groin.

Figure 3:
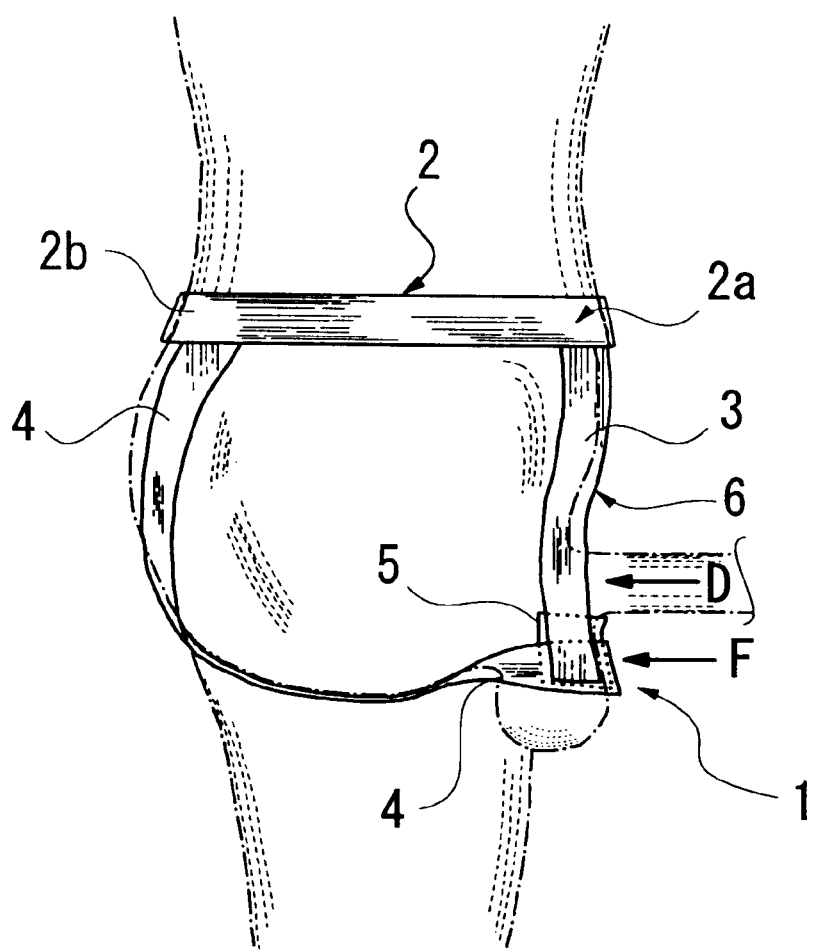
FIG. 3 is a schematic side elevational view of the phimosis curing appliance as illustrated in FIGS. 1 and 2, a state being shown in that the phimosis curing appliance is put on a human body.

FIG. 3 is a schematic side view showing a condition in that the phimosis curing appliance 1 is attached to the patient.

The waist holding belt 2 slightly stretched in the diametrical direction is wound around the patient's waist portion in a slightly tensioned state. When the belt 2 is positioned on the patient's waist in place, it is in intimate contact with the waist portion under the resiliently restoring force of the materials so that the phimosis curing appliance 1 is suitably fitted on the waist. The patient's penis extends through the gap 6 between the left and right supporting belts 3 while spreading the gap 6. The traction belts 4, which extends to the rear portion 2b of the waist holding belt 2 through the patient's groin and buttock, are slightly stretched and tensioned between the lower ends of the supporting belts 3 and the rear portion 2b to pull the supporting belts 3 into the patient's groin, thereby biasing the strip 5 on the lower end portions of the belts 3 backward of the patient's body so as to draw the patient's scrotum into his groin. In other words, the strip 5 abuts against the skin of the scrotum to urge it backward of the patient's body, so that the scrotal skin backwardly draws the prepuce of the penis continuous to the scrotal skin.

Thus, the surplus prepuce of the patient's penis is urged toward a root of the penis as shown by arrow D in FIG. 3, and it is drawn toward the patient's groin under the tension of the scrotal skin. As a result, the glans of the patient's penis is surely and completely exposed.

According to the phimosis curing appliance 1 having the aforementioned arrangement, the prepuce of the patient's penis extending through the gap 6 between the supporting belts 3 can be biased toward the root of the patient's penis by its contact with the belts 3 when the phimosis curing appliance 1 is put on the human body. In addition, the skin of the scrotum is drawn toward the root of the penis (backwardly of the human body), since the scrotum urging force F of the strip 5 shown in FIG. 3 acts to bias the scrotum into the human groin. As a result, the surplus prepuce of the penis is drawn toward the root of the penis and stretched over the penis root region to keep the glans of penis in an exposed condition. The phimosis curing appliance 1 maintains the scrotum to be biased until the phimosis curing appliance 1 is removed from the human body. Therefore, the surplus prepuce of penis is held in the root region of penis until the scrotum biasing force F is released. Thus, the glans of penis continues to be exposed for a relatively long time.

The phimosis curing appliance 1 allows the surplus prepuce of penis to be retracted toward the root thereof, and this enables the glans of penis to be completely exposed for a relatively long time, without need of any medical treatment such as prepuce excision or the like. In addition, such an uncovered glans allows the patient to psychologically overcome the inferiority complex due to the phimosis and effect his physiological ability sufficiently without deteriorating his personality. Further, according to the phimosis curing appliance 1, the glans of penis is exposed only when the phimosis curing appliance 1 is put on the patient, whereas it is usually covered with the prepuce to be protected. However, once the phimosis curing appliance 1 is attached on the patient, the supporting belts 3 and the scrotum biasing strip 5 urge the underbelly and penis root of the patient to expose the entire penis forwardly. Thus, the effective length of the patient's penis is substantially increased. Accordingly, the phimosis curing appliance 1 of the aforementioned structure is extremely advantageous in practice, since it is extremely low in cost and provides an unthought practical advantage in comparison to a medical treatment, e.g., prepuce excision operation which may substantially shorten the penis. The drawing action of the supporting, traction and scrotum biasing belts 3, 4, 5 provide an appropriate tension on the skin of the scrotum and an appropriate pressure on the root portion of the penis while completely exposing the glans of penis. Therefore, the phimosis curing appliance 1 can provide secondary advantages, such as the increased hardness of the patient's penis, the improved sensitivity of the patient's penis and the prolonged erection of the penis, irrespective of whether he has a pseudophimosis symptom.

Figure 4A:
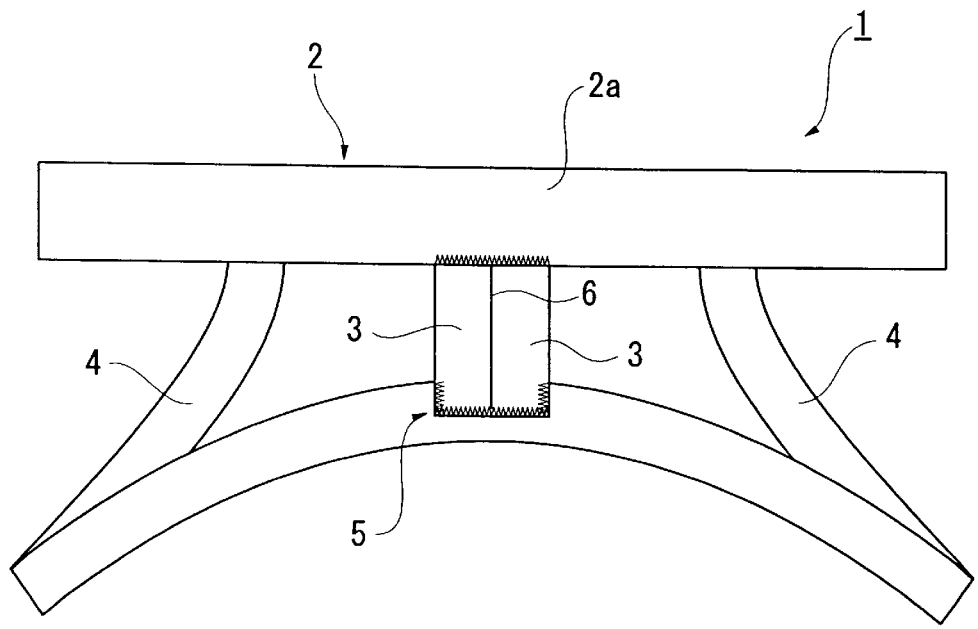
FIGS. 4(A) and (B) are front and rear elevational views of a phimosis curing appliance according to another embodiment of the present invention.
Figure 4B:
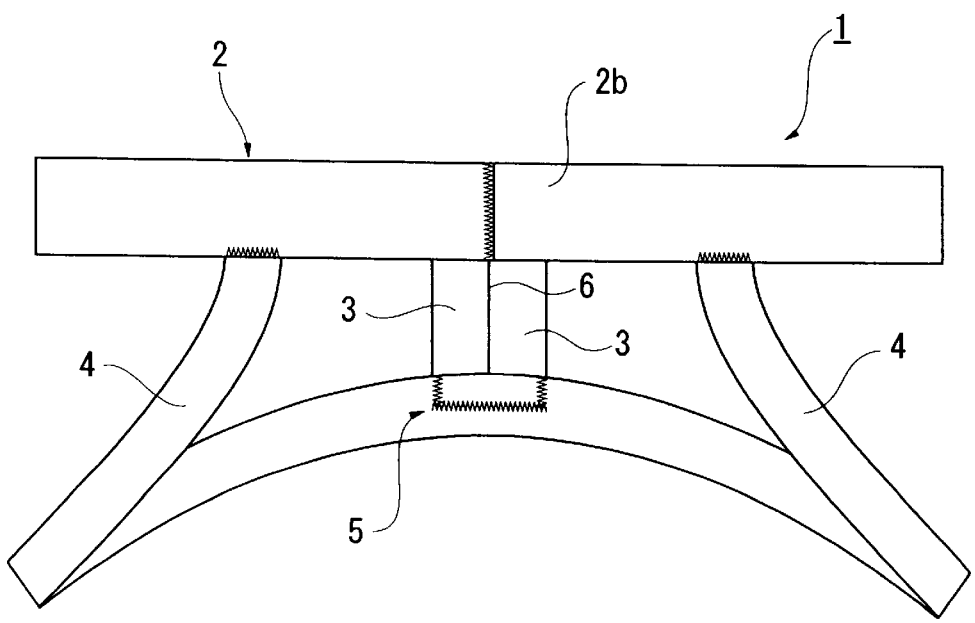
Figure 5A:
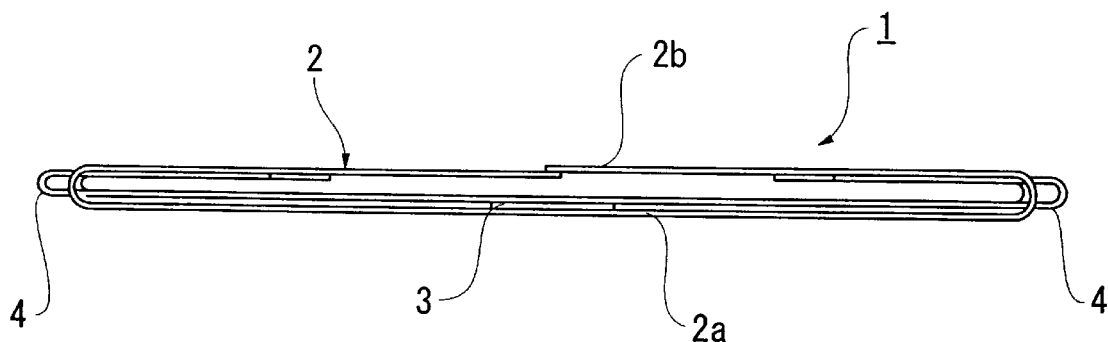
FIGS. 5(A)–(D) are plan, right-side, left-side and bottom views of the phimosis curing appliance as illustrated in FIG. 4.
Figure 5B:
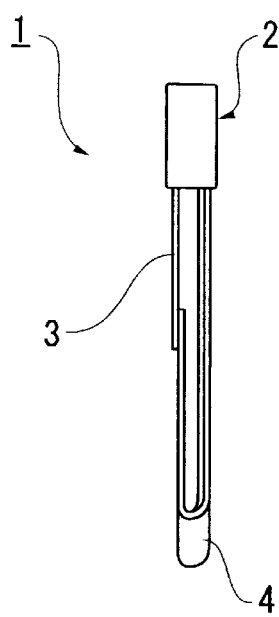
Figure 5C:
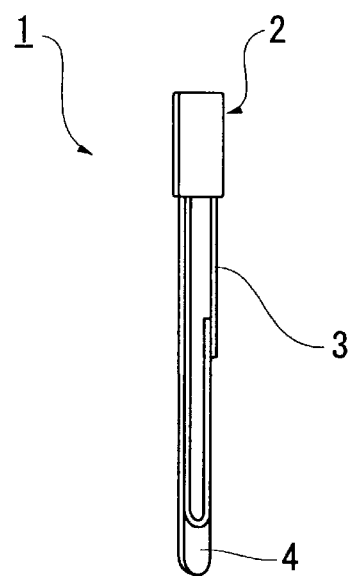
Figure 5D:
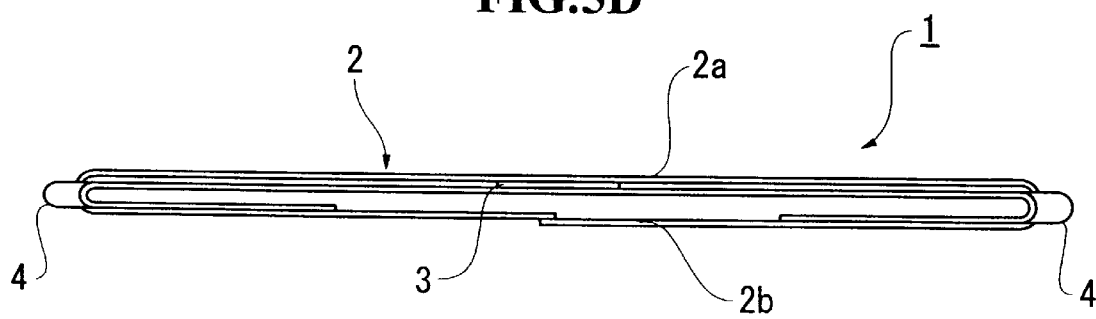

FIG. 4A is a front view of another embodiment of a phimosis curing appliance according to the present invention, and FIG. 4B is a rear elevational view thereof. FIG. 5A is a plan view of the phimosis curing appliance shown in FIG. 4; FIG. 5B is a right-hand side view of the same; FIG. 5C is a left-hand side view of the same; and FIG. 5D is a bottom view of the same. In FIGS. 4 and 5, the elements or constituents identical with those of the previously mentioned embodiment are indicated by the same reference numerals.

The phimosis curing appliance shown in FIGS. 4A–4B and 5A–5D and 5 generally has an arrangement equivalent to that of the previous embodiment. The phimosis curing appliance 1 of this embodiment, however, differs in that the scrotum biasing belt 5 is formed by a connection or junction of the supporting belts 3 and the traction belts 4. The supporting and traction belts 3, 4 are made of substantially the same resilient fabric as in the first embodiment, whereas the waist holding belt 2 is made of a relatively stretchable and resilient fabric having its stretchability higher than those of the belts 3, 4. When the phimosis curing appliance 1 is put on the patient, the traction belts 4 are stretched to an extent that they draw the scrotum biasing zone 5 (the connection area of the belts 3, 4) and the supporting belts 3 into the patient's groin under its resiliently restoring force.

The gap 6 formed between the supporting belts 3 is slightly divergent in its upward direction. For example, the gap 6 is set to be equal to or smaller than about 2 mm at its lowermost end, while the gap 6 is set to have the width ranging from approximately 5 to 15 mm at its uppermost end.

Figure 6A:
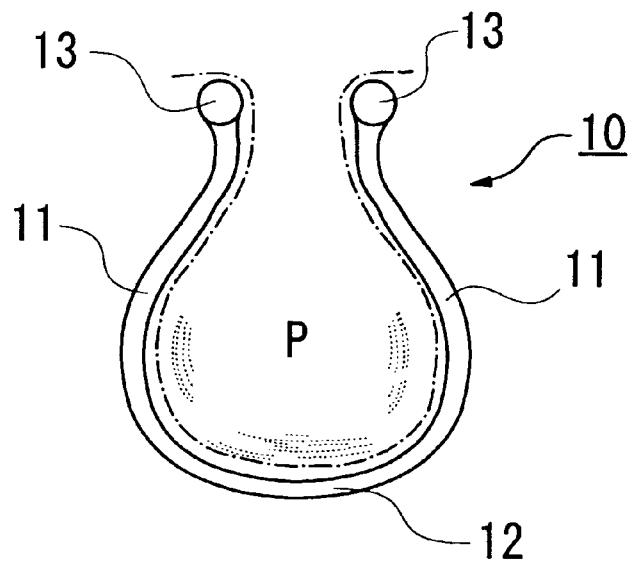
FIGS. 6(A) and (B) are schematic side views of phimosis curing appliances according to the other embodiments of the present invention.
Figure 6B:
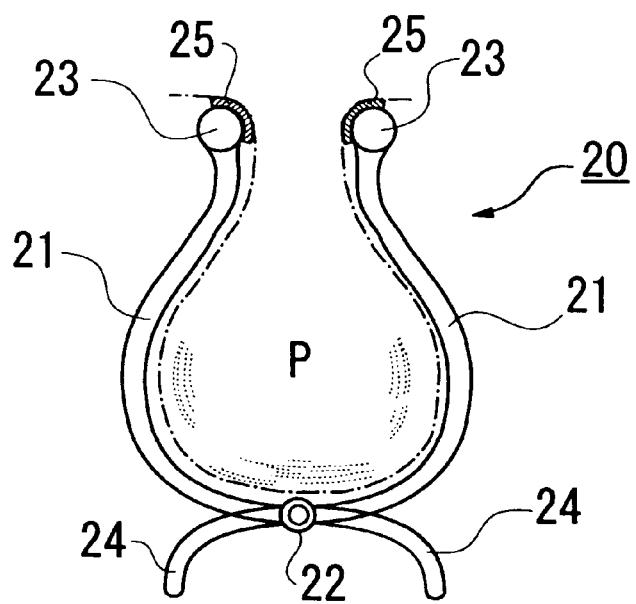

FIGS. 6A and 6B are schematic side views showing alternative embodiments of a phirnosis curing appliance according to the present invention.

Referring to FIGS. 6A and 6B, there are shown phimosis curing appliances 10 and 20, each having an arrangement for holding the root portion of the patient's scrotum from the front and back sides of the patient's body to draw the surplus prepuce of the patient's penis toward the root thereof.

The phimosis curing appliance 10 shown in FIG. 6A comprises a pair of resiliently deformable arms 11 which are molded to have an outline substantially complementary to a profile of the patient's scrotum P. The arms 11 are interconnected to each other by a joint portion 12. The joint portion 12 has a desired resiliency sufficient for separating the arms 11 from each other. The top end of each of the arms 11 is formed with a spherical enlarged abutment portion 13. These abutment portions 13 function to resiliently grasp the root portion of the patient's scrotum by resilient deformation of the arms 11 and the joint portion 12. Thus, the skin of the patient's scrotum and particularly the scrotum skin positioned in the front of the patient's body are pulled toward the patient's groin so as to draw the surplus prepuce of the patient's penis toward the root thereof.

The phimosis curing appliance 20 shown in FIG. 6B comprises arms 21 and abutment portions 23, which have structures and functions similar to those elements 11, 13 of the phimosis curing appliance 10. However, the base ends of the arms 21 are pivotally interconnected by a hinge or pivot means 22. The hinge means 22 includes an elastic member (now shown), such as leaf spring or coil spring. The elastic member functions to control the pivotal motion of the arms 21. The hinge means 22 is adapted to bias the abutment portions 23 inward of the phimosis curing appliance 20 so that the abutment portions 23 is moved toward each other.

In use, the patient pinches the extensions 24 of the arm portions 11 with his fingers and causes the arms 21 to outwardly pivot to separate the abutment portions 23 from each other. Thereafter, the patient releases the extensions 24 so that the abutment portions 23 resiliently grasp the root portion of the patient's scrotum under the restoring force of the hinge means 22. Each of the abutment portions 23 has a soft coating material 25 resiliently engageable with the skin of the patient's scrotum, such as soft plastic, woven fabric or non-woven fabric. The coating material 25 draws the skin of the patient's scrotum inwardly into the patient's groin to move the surplus prepuce of the patient's penis toward the root thereof by the tension of the scrotum skin.

Although specific preferred embodiments have been described with reference to the drawings, the present invention is not limited to such embodiments, but may be modified and changed without departing from the scope of the invention as claimed in the attached claims.

INDUSTRIAL APPLICABILITY

According to the phimosis curing appliances of the present invention, the surplus prepuce of the pseudophimosis is forcedly retracted toward the root of the human penis so that the glans of the penis can be surely kept in an exposed condition for a long time. In addition, the phimosis curing appliances are of a simplified structure suitable for standardization and mass production.

What is claimed is:

1. A phimosis curing appliance comprising an annulus waist holding belt supportable on a human waist; a resiliently stretchable supporting belt suspended from the waist holding belt to form a region through which a human penis extends; a resiliently stretchable traction belt for connecting a rear portion of the waist holding belt and the supporting belt; and a scrotum biasing zone provided in a joint area of the supporting belt and the traction belt, the upper end portion of the supporting belt being connected to the waist holding belt and the scrotum biasing zone being drawn inward of the human groin by the traction belt.

2. A phimosis curing appliance as defined in claim 1, wherein a pair of said supporting belts extend between said waist holding belt and said traction belt, and wherein said supporting belts form a gap defining said region through the penis extends.

3. A phimosis curing appliance as defined in claim 2, wherein said gap is slightly divergent in its upward direction.

4. A phimosis curing appliance as defined in claim 2, wherein the size of said gap is set to be equal to or smaller than 2 mm.

5. A phimosis curing appliance as defined in claim 1 wherein said scrotum biasing zone is formed by a connection between said supporting belt and said traction belt.

6. A phimosis curing appliance as defined in any one of claims 1 to 5, wherein said supporting and traction belts are made of substantially the same resilient material, and wherein the resilient stretchability of the supporting and traction belts is limited to be lower than that of said waist holding belt.

* * * * *